United States Patent [19]

Center

[11] Patent Number: 5,311,632
[45] Date of Patent: May 17, 1994

[54] ULTRASONIC PLAQUE REMOVAL DEVICE

[76] Inventor: Leslie T. Center, P.O. Box FL 284, Smith's Parish FL BX, Bermuda

[21] Appl. No.: 61,617

[22] Filed: May 12, 1993

[51] Int. Cl.⁵ ..................... A61C 17/34; A46B 13/02
[52] U.S. Cl. ..................................... 15/22.1; 433/216
[58] Field of Search ............... 15/22.1, 22.2; 433/216

[56] References Cited

U.S. PATENT DOCUMENTS

| | | | |
|---|---|---|---|
| 3,466,689 | 9/1969 | Aurelio et al. | 15/22.1 |
| 3,685,080 | 8/1972 | Hubner | 15/22.1 |
| 5,150,492 | 9/1992 | Suroff | 15/22.1 |
| 5,247,716 | 9/1993 | Bock | 15/22.1 |

*Primary Examiner*—Edward L. Roberts
*Attorney, Agent, or Firm*—Richard L. Miller

[57] ABSTRACT

A device for removing plaque from teeth comprises a toothbrush having a thick, cylindrical, hollow handle in which are located an electric motor actuable to cause rotation of an eccentrically mounted member and vibration of the entire device, and an ultrasonic transducer actuable to produce high frequency sound waves along the brush. The combination of brush vibration and ultrasound loosens and removes plaque from the teeth.

8 Claims, 1 Drawing Sheet

U.S. Patent      May 17, 1994      5,311,632
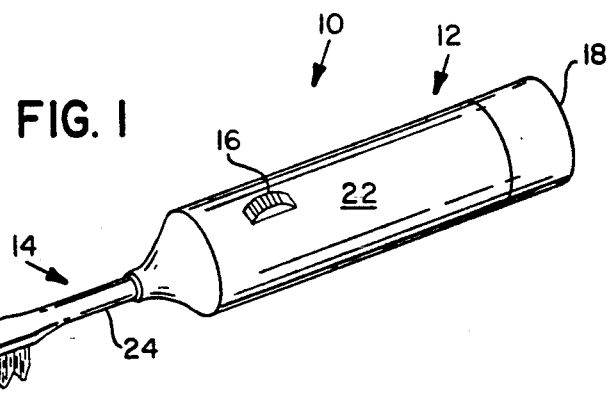
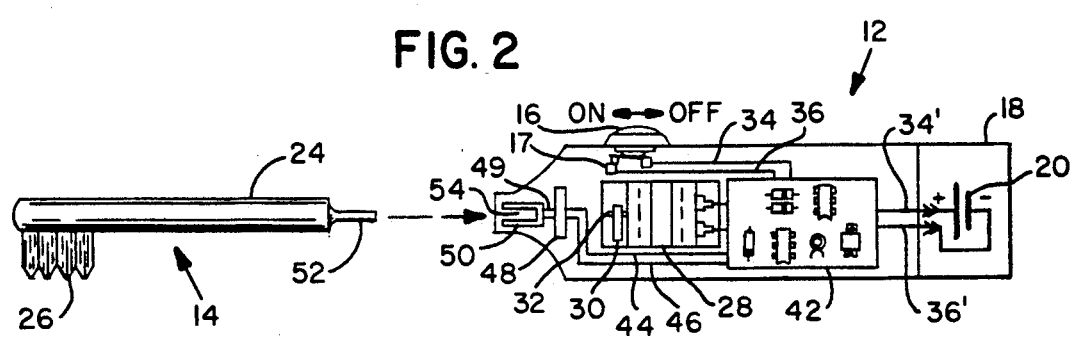
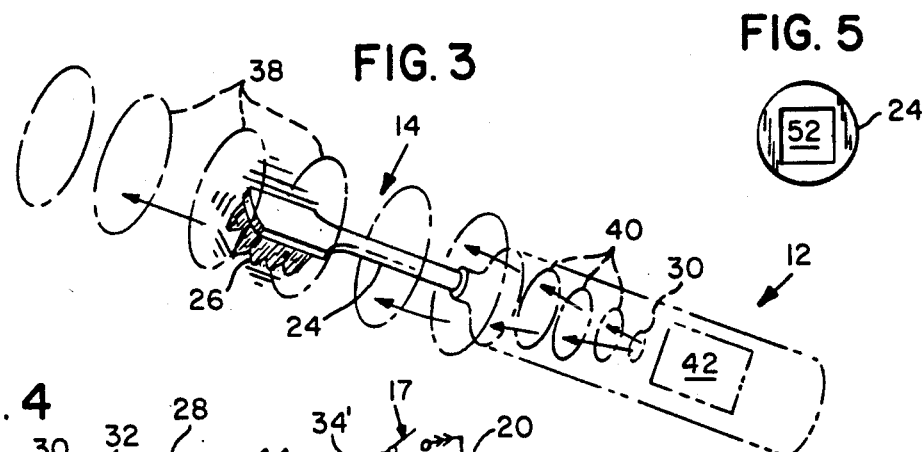
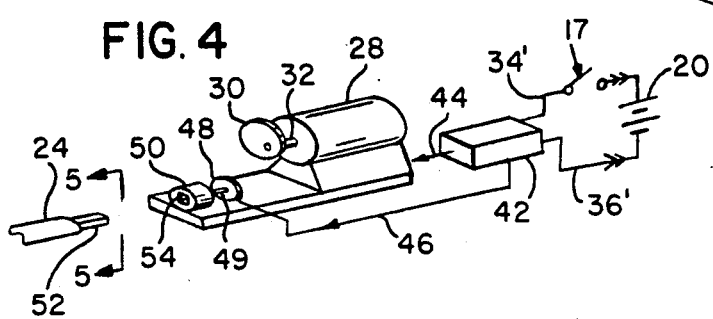

ULTRASONIC PLAQUE REMOVAL DEVICE

BACKGROUND OF THE INVENTION

1. Field of the Invention

This invention relates to an improved plaque removal device for teeth consisting of a toothbrush which vibrates and generates in the brush portion an ultrasonic wave to assist in loosening plaque.

2. Description of the Prior Art

The present invention combines the capability of ultrasonic or high frequency sound waves to clean objects including teeth, with vibratory motion similar to that of an electric toothbrush, to produce an improved device for removing plaque from teeth.

Ultrasonic sound wave vibrations above 20 KHz are generally produced by a transducer containing a piezoelectric or similar substance such as a quartz crystal oscillator which converts high frequency electric current to into vibrating ultrasonic waves. Ultrasound has found wide industrial use, particularly in the nondestructive testing of manufactured objects and the cleaning of many objects. Cleaning is often accomplished by immersing the object into a cleaning liquid into which ultrasonic waves are propagated, with the cavitating liquid removing film or dirt even from inaccessible regions. In medicine, ultrasound has been used to examine organs without surgery, and has been found to be far safer than x-rays.

Ultrasonics has also been applied to the cleaning of teeth. The removal of plaque is important to good dental health. Plaque is a thin, colorless, sticky film that constantly forms on the teeth. When foods containing sugars and starches are eaten, the bacteria in plaque produces acids which attack tooth enamel. The stickiness of the plaque keeps these acids in contact with teeth. After many such attacks, the enamel breaks down and a cavity forms.

If plaque is not removed by daily brushing, flossing or other techniques, it hardens into calculus (tartar). As calculus forms near the gumline, gums can become irritated and inflamed. They become swollen and may bleed. The gums begin to pull away from the teeth and form pockets that may become infected. If this gum disease is not treated promptly, the bone supporting the teeth is destroyed and healthy teeth may be lost.

Many prior art devices use ultrasound to remove plaque from teeth. In U.S. Pat. No. 5,013,241 to von-Gutfeld et al., a dental tool is shown for cleaning plaque from teeth by focusing an ultrasound wave into a jet of liquid such as water which is then directed as a stream upon the teeth.

Other devices use ultrasonic energy in periodontics. Commercially available units incorporate a solid metal tip to which appropriate ultrasonic energy is applied. The vibrating metal tip is used to contact the surface of a tooth in order to remove plaque therefrom. Because of heat buildup, cooling and rinsing water flows are normally used in association with the metal tip. Such devices can be uncomfortable due to the high intensity vibrations produced, which can cause nerve pain. High pitched audible sounds are generated and can be uncomfortable. Devices of this type are primarily dentist's tools and cannot be used at home.

Other prior art devices utilizing ultrasonics are U.S. Pat. No. 4,920,954 to Alliger et al. in which a solid titanium wire is inserted into the artery of a human, and ultrasound vibrations are applied to the wire to produce a cavitation force for the removal of plaque from the artery. U.S. Pat. No. 4,944,296 to Suyama incorporates a piezoelectric element into the handle of a toothbrush, the bending of the handle which occurs during normal tooth brushing causing the generation of electrons which remove that dental plaque which is charged with positive electricity.

The present invention provides a unique plaque removal device consisting of a toothbrush having an electric motor in the handle thereof causing rotation of an eccentric member which produces rotational vibration of the entire toothbrush. Also in the handle is an ultrasonic transducer which produces ultrasonic waves that are coupled into the brush portion of the toothbrush and are propagated from the brush portion non-directionally in the mouth. The combination of the rotational vibration of the brush and the production of the standing ultrasonic waves provides improved tooth cleaning capability.

Because the device of this invention does not suffer from the disadvantages of the ultrasonically vibrating metal tip devices, it can safely be used a home as part of a person's every day routine of tooth brushing. It provides considerable advantages over brushing with a standard or even an electric toothbrush because the vibrations of the brush combined with the generation of the ultrasonic waves loosens the plaque in places that are normally not reached by standard toothbrushes. This results in considerably cleaner, plaque free teeth and prevents gum disease and bone loss. The vibrations of the brush will more easily remove plaque from teeth where the plaque has previously been loosened by the ultrasonic waves. The ultrasonic waves are not focused and are general to the entire region about the brush in which the standing wave is produced. The waves will be more apparent at the end of the brush which vibrates more freely, particularly if the ultrasonic wave length is advantageously selected to correspond to the length of the brush portion. The combined action of the rotational vibration and the ultrasonic waves will be far more effective than brushing alone, or brushing combined with flossing, in loosening and removing plaque from teeth.

It is therefore an object of this invention to produce a unique plaque removal device which comprises a vibrating toothbrush in combination with the generation and propagation of ultrasonic waves along the brush portion of the toothbrush.

Another object of this invention is a toothbrush that vibrates in a rotational manner, and which contains an ultrasonic transducer generating high frequency sound waves in the toothbrush in order to loosen plaque.

A further object of this invention is a toothbrush having a battery driven motor causing rotation of an eccentric member producing rotational vibration of the entire toothbrush, and an ultrasonic transducer coupled to the toothbrush which generates ultrasonic waves therein.

A still further object of this invention is a vibrating toothbrush in which an ultrasonic transducer generates high frequency sound waves to loosen plaque on the teeth.

DESCRIPTION OF THE DRAWINGS

FIG. 1 is a diagrammatic perspective view of the present invention;

FIG. 2 is a diagrammatic view illustrating the internal components of the invention;

FIG. 3 is a diagrammatic view illustrating the vibration pattern of this invention;

FIG. 4 is a diagrammatic pictorial block diagram illustrating the internal components of this invention; and FIG. 5 is a cross sectional view along line 5—5 of FIG. 4.

DETAILED DESCRIPTION OF THE PREFERRED EMBODIMENTS

In accordance with a preferred embodiment of this invention where similar reference numerals denote similar elements throughout the drawings, there is shown in FIG. 1 a toothbrush device 10 having a thick cylindrical hollow handle 12 to which is connected a removable brush portion 14. The use of separable components for device 10 permits each member of the family to use the invention and have their personal brush portion.

On handle 12 is conveniently located a thumb-movable member 16 which, when moved to the 'on' position, actuates an electrical switch 17 to turn on the device 10. Moving the member 16 to its other position turns the device 10 off.

Handle 12 has a removable end portion 18 which contains a replaceable battery 20. The outside case 22 of handle 12 is preferably of strong plastic to withstand hard use and being dropped on a bathroom floor. The neck 24 of brush portion 14 may also be composed of plastic, and the neck 24 may have a metallic rod inserted therein to assist in the generation of high frequency sound waves therethrough as will be described. Bristles 26 are attached at one end of brush portion 14.

Contained within the hollow center of handle 12 is an electric motor 28 to which is attached an eccentrically mounted member 30 via a rotatable shaft 32. Motor 28 is connected via switch 17 and electrical conductors including lines 34, 34', 36 and 36' to battery 20, so that moving member 16 to the on position closes switch 17 by moving a spring loaded conducting member to close the electrical circuit. Motor 28 will rotate eccentric member 30 and the entire device 10 will vibrate in a rotary direction as shown by the plurality of circles 38 in FIG. 3. Because the mass of handle 12 is so much greater than that of brush portion 14, and handle 12 is held in the hand of a user, the bristled end of brush portion 14 will vibrate about a greater radius (circles 38) than the handle 12 (circles 40).

Also connected to battery 20 is an electronics package 42 of standard construction producing high frequency oscillations which are coupled via lines 44, 46 to an ultrasonic transducer 48. The transducer 48 is in turn mechanically coupled via connector 49 to a holder 50 which is adapted to surround and frictionally secure within it an extension 52 as rectangular in cross-section, and slidable within an opening 54 in holder 50. As a result the brush portion 14 can be easily inserted into and removed from holder 50 to replace one brush portion 14 with another.

The ultrasonic transducer 48 is preferably a commercially available device capable of producing an ultrasonic wave in the frequency range of 10-20 MHz. The energy is coupled directly from the transducer 48 through a connector 49 which acts as a wave guide and into holder 50 from which it propagates into the handle 24 of brush portion 14. The ultrasonic energy, which is sufficient to cause vibration of brush portion 14 without overheating, is propagated as a moving wave in a non-focused manner throughout the mouth of the user.

It is preferred that a plaque softening or tooth polishing liquid or gel be applied to the teeth prior to use of the toothbrush. The ultrasonic energy coupled into the brush portion 14 serves to soften or remove plaque from the teeth as the wave is propagated in the mouth. The liquid or gel surrounding the teeth will respond to the ultrasonic energy by vibrating and producing cavitation, assisting in the loosening of the plaque and helping to carry it away from the teeth. Medical research has shown that ultrasound or cavitation resulting from ultrasound has little detrimental effect on tissue, bone or cartilage, but will remove plaque from teeth and blood vessels.

In addition to the ultrasonic loosening of the plaque, the brush vibration caused by the motor driven eccentric member 30 will, in conjunction with the polishing liquid or gel, also assist in removing or loosening plaque from the teeth. The combination of brush vibration and the propagation of ultrasonic waves in the mouth is considerably more efficient at removing plaque than brushing alone, or brushing and flossing.

While the invention has been described with respect to preferred embodiments thereof, it is apparent that changes can be made to the structure and arrangement of its elements without departing from the scope of the invention as hereinafter claimed.

What is claimed is:

1. An ultrasonic plaque removal device for removing plaque from teeth comprising:
   a) a toothbrush device having a hollow grip portion and a brush portion extending from and being separable from said brush portion, said toothbrush device having a central axis extending through said brush portion and said grip portion;
   b) first means located within said grip portion for creating a rotational vibration of said toothbrush device about said central axis; and
   c) second means located within said grip portion connected with and producing an ultrasonic wave within said brush portion.

2. An ultrasonic plaque removal device as in claim 1 wherein said first means comprises an electric motor connected with and operable to produce rotation of an eccentric member.

3. An ultrasonic plaque removal device as in claim 2 wherein said second means comprises:
   a) electrical circuit means for generating a high frequency electrical signal;
   b) a piezoelectric element receiving said high frequency electrical signal and generating an ultrasonic sound wave; and
   c) coupling means for coupling said ultrasonic wave to said brush portion to produce ultrasonic vibration of said brush portion.

4. An ultrasonic plaque removal device as in claim 3 wherein said brush portion comprises a flat handle with a plurality of bristles connected at one end and a narrow rectangular extension at the other end thereof.

5. An ultrasonic plaque removal device as in claim 4 in which said coupling means comprises:
   a) a holder having a rectangular shaped receptacle therein adapted to receive therein and hold securely the extension of said flat handle; and
   b) wave transmitting means connecting said piezoelectric element to said holder whereby the ultrasonic waves are coupled from said piezoelectric element to said brush portion.

6. An ultrasonic plaque removal device as in claim 5 and including an electrical battery located within said grip portion, and circuit means including a switch means connecting said battery with said electric motor and with said circuit means to provide electrical power thereto.

7. An ultrasonic plaque removal device as in claim 6 in which said switch means comprises a manually operable element mounted on the outside of said grip portion and movable between on and off positions, and an electrical connector means in said circuit means and adapted to move and close said circuit when said manually operable element is in its on position.

8. An ultrasonic plaque removal device as in claim 7 in which said grip means has a removable end portion at the end opposite the said brush portion for providing access to said battery.

* * * * *